US009087678B2

(12) United States Patent
Kakutani et al.

(10) Patent No.: US 9,087,678 B2
(45) Date of Patent: Jul. 21, 2015

(54) ION SOURCE, HEAVY PARTICLE BEAM IRRADIATION APPARATUS, ION SOURCE DRIVING METHOD, AND HEAVY PARTICLE BEAM IRRADIATION METHOD

(71) Applicant: Kabushiki Kaisha Toshiba, Tokyo (JP)

(72) Inventors: Akiko Kakutani, Kanagawa (JP); Kiyoshi Hashimoto, Kanagawa (JP); Kiyokazu Sato, Tokyo (JP); Takeshi Yoshiyuki, Kanagawa (JP); Tsutomu Kurusu, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 58 days.

(21) Appl. No.: 13/771,818

(22) Filed: Feb. 20, 2013

(65) Prior Publication Data

US 2013/0234036 A1 Sep. 12, 2013

(30) Foreign Application Priority Data

Mar. 8, 2012 (JP) .................................. 2012-051577

(51) Int. Cl.
*H01J 49/16* (2006.01)
*H05H 1/46* (2006.01)
(Continued)

(52) U.S. Cl.
CPC ............. *H01J 37/3299* (2013.01); *H01J 27/24* (2013.01); *H01J 37/30* (2013.01); *H01J 37/32972* (2013.01); *A61N 5/1067* (2013.01); *A61N 2005/1088* (2013.01); *H01J 37/32935* (2013.01); *H01J 49/161* (2013.01); *H01J 2237/0815* (2013.01); *H05H 1/46* (2013.01)

(58) Field of Classification Search
CPC .............. H01J 27/24; H01J 37/32935; H01J 37/32917; H01J 37/32972; H01J 37/32981; H01J 37/3299
See application file for complete search history.

(56) References Cited

U.S. PATENT DOCUMENTS 3,849,656 A * 11/1974 Wallington .................... 250/424
3,919,664 A * 11/1975 McAllister ...................... 372/95
(Continued)

FOREIGN PATENT DOCUMENTS

JP 62-061258 3/1987
JP 09-106779 4/1997
(Continued)

OTHER PUBLICATIONS

Bulgakova et al., "Double Layer Effects in Laser-Ablation Plasma Plumes", Physical Review E, vol. 62, No. 4, Oct. 2000.*
(Continued)

*Primary Examiner* — Nicole Ippolito
*Assistant Examiner* — James Choi
(74) *Attorney, Agent, or Firm* — Oblon, McClelland, Maier & Neustadt, L.L.P.

(57) ABSTRACT

A laser-ablation plasma generator generates laser-ablation plasma from a target in a vacuum vessel. An ion beam extractor generates an ion beam by extracting ions included in the laser-ablation plasma from the vacuum vessel. An ion detector detects unintended ions other than intended ions, which are obtained by ionizing the elements in the target, out of ions in the vacuum vessel and outputs a detection signal representing a value which is a number of the unintended ions or a mixing ratio of the unintended ions to the intended ions as a detection result. The ion source using the laser beam makes it possible to normally monitor unintended ions other than intended ions out of ions in the vacuum vessel.

13 Claims, 11 Drawing Sheets

(51) Int. Cl.
*H01J 37/32* (2006.01)
*H01J 27/24* (2006.01)
*H01J 37/30* (2006.01)
*A61N 5/10* (2006.01)

(56) References Cited

U.S. PATENT DOCUMENTS

| | | | |
|---|---|---|---|
| 5,111,053 A * | 5/1992 | Suzuki | 250/424 |
| 8,822,948 B1 * | 9/2014 | Hartwell | 250/424 |
| 2005/0139763 A1 * | 6/2005 | Nagai et al. | 250/287 |
| 2008/0006769 A1 * | 1/2008 | Staats | 250/288 |
| 2008/0203287 A1 * | 8/2008 | Crawford | 250/282 |
| 2008/0272286 A1 * | 11/2008 | Vestal | 250/282 |
| 2010/0012831 A1 * | 1/2010 | Vertes et al. | 250/282 |
| 2012/0085904 A1 * | 4/2012 | Schwieters et al. | 250/282 |
| 2013/0207000 A1 * | 8/2013 | Gunther et al. | 250/396 R |
| 2014/0225000 A1 * | 8/2014 | Kakutani et al. | 250/423 P |

FOREIGN PATENT DOCUMENTS

| | | |
|---|---|---|
| JP | 3713524 | 9/2005 |
| JP | 2009-37764 | 2/2009 |

OTHER PUBLICATIONS

Office Action issued Apr. 30, 2014, in Japanese Patent Application No. 2012-051577, filed Mar. 8, 2012.

Hirotsugu Kashiwagi, et al., "Acceleration of High Current and Highly Charged Carbon Beam Using Direct Injection Scheme", Japan Atomic Energy Research Institute, 3 pages.

* cited by examiner

ION SOURCE, HEAVY PARTICLE BEAM IRRADIATION APPARATUS, ION SOURCE DRIVING METHOD, AND HEAVY PARTICLE BEAM IRRADIATION METHOD

CROSS-REFERENCE TO RELATED APPLICATION

This application is based upon and claims the benefit of priority from Japanese Patent Application No. 2012-051577, filed on Mar. 8, 2012, the entire content of which is incorporated herein by reference.

FIELD

The embodiments of the present invention relate to an ion source that generates an ion beam by irradiation with a laser beam, a heavy particle beam irradiation apparatus, an ion source driving method, and a heavy particle beam irradiation method.

BACKGROUND

An ion source is known as an apparatus generating an ion beam by irradiation with a laser beam. An ion source increases energy of ions and outputs as an ion beam to an external device. An example of the external device is a heavy particle beam irradiation apparatus used for cancer treatment. A heavy particle beam irradiation apparatus is an apparatus accelerating an ion beam and irradiating a target site with the accelerated ion beam as a heavy particle beam. For example, carbon ions are used as the ions and, particularly, $C^{6+}$ ions are used for cancer treatment.

For example, an ion source may employ a method using microwave discharge plasma and a method using a laser beam (for example, see Japanese Patent No. 3713524 and Japanese Patent Application Laid-Open No. 2009-37764, the entire content of which is incorporated herein by reference).

An ion source using a laser beam irradiates the surface of a target in a vacuum vessel with a laser beam and vaporizes and ionizes elements of the target with the energy of the laser beam to generate plasma (laser-ablation plasma). Ions included in the laser-ablation plasma are extracted from the vacuum vessel, and the extracted ions are accelerated at the time of extraction to generate an ion beam. The ion source using a laser beam can generate multi-charged ions such as $C^{6+}$ ions by adjusting the energy and density of the laser beam.

In the ion source using a laser beam, unintended ions other than intended ions ($C^{6+}$ ions) may be mixed in a vacuum vessel for the following reasons. For example, when moisture or particles are attached to a target, ions of contaminants (such as hydrogen molecular ion ($H_2+$) and $O^{8+}$ ions) may be mixed as unintended ions in the vacuum vessel. When residual gas is present in the vacuum vessel, ions of residual gas components may be mixed as unintended ions in the vacuum vessel. When unintended ions are mixed in the vacuum vessel, the unintended ions in addition to intended ions are extracted from the vacuum vessel and are output as an ion beam.

BRIEF DESCRIPTION OF THE DRAWINGS

The above and other features and advantages of the present invention will become apparent from the discussion hereinbelow of specific, illustrative embodiments thereof presented in conjunction with the accompanying drawings, in which.

DETAILED DESCRIPTION

Figure 1:
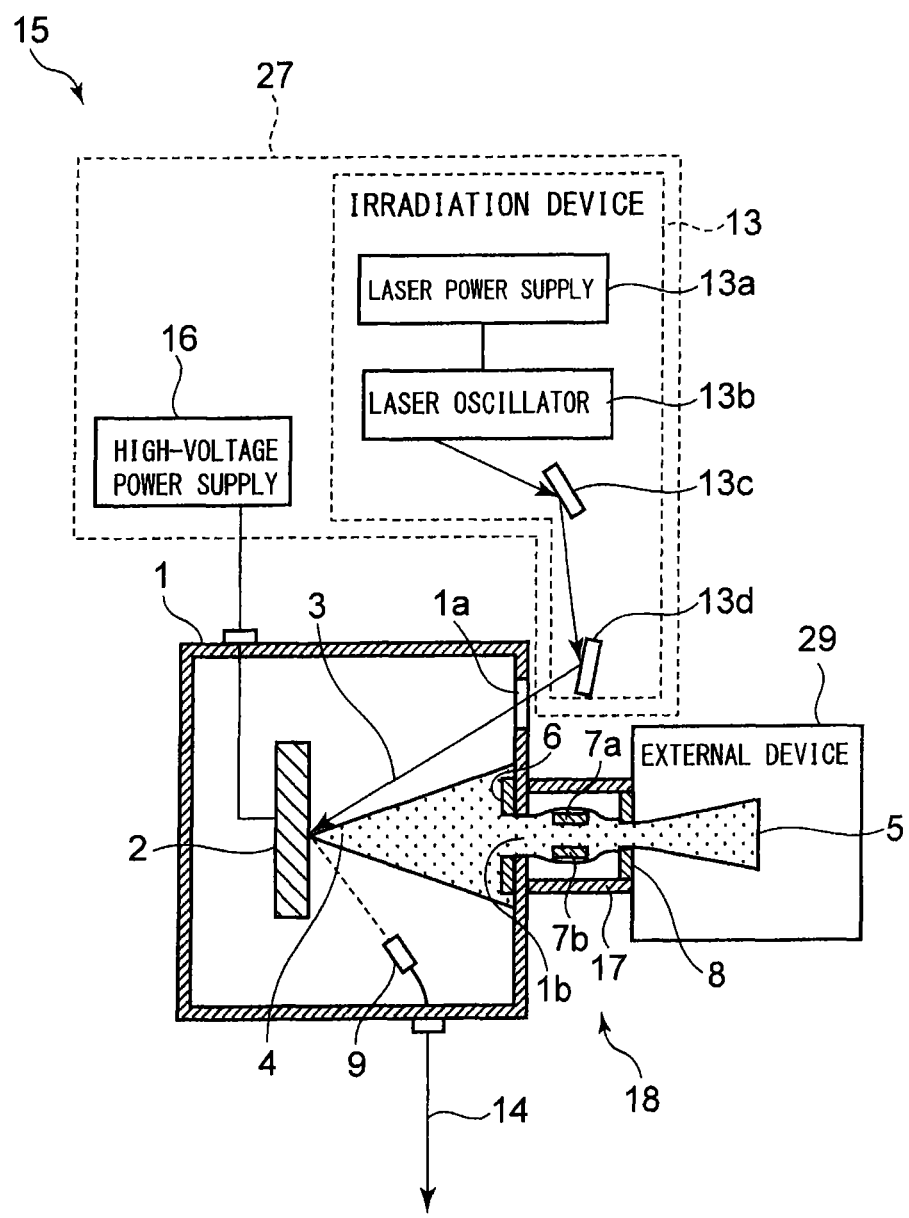
FIG. 1 is a cross-sectional view schematically illustrating the configuration of an ion source according to a first embodiment of the invention.

An object of the embodiments of the present invention is to normally monitor unintended ions other than intended ions out of ions in a vacuum vessel.

According to an embodiment of the invention, there is provided an ion source comprising: a laser-ablation plasma generator that generates laser-ablation plasma from a target in a vacuum vessel; an ion beam extractor that generates an ion beam by extracting ions included in the laser-ablation plasma from the vacuum vessel; and an ion detector that detects unintended ions other than intended ions, which are obtained by ionizing elements of the target, out of ions in the vacuum vessel and that outputs a detection signal representing a value which is a number of the unintended ions or a mixing ratio of the unintended ions to the intended ions as a detection result.

According to another embodiment of the invention, there is provided a heavy particle beam irradiation apparatus comprising: at least one ion source; and an ion beam accelerator that accelerates an ion beam from the at least one ion source and outputs an accelerated ion beam as a heavy particle beam to irradiate a target site, wherein the at least one ion source each includes: a laser-ablation plasma generator that generates laser-ablation plasma from a target in a vacuum vessel in response to an operation instructing signal and stops the generation of the laser-ablation plasma in response to a stop instructing signal, an ion beam extractor that generates the ion beam by extracting ions included in the laser-ablation plasma from the vacuum vessel, an ion detector that detects unintended ions other than intended ions, which are obtained by ionizing elements of the target, out of the ions in the vacuum vessel and outputs a detection signal representing a value, which is a number of the unintended ions or a mixing ratio of the unintended ions to the intended ions, as a detection result, and an operation-control signal processing circuit that outputs the operation instructing signal to the at least one laser-ablation plasma generator and outputs the stop instructing signal to the at least one laser-ablation plasma generator when the value of the detection signal output from the ion detector is greater than a threshold value.

According to another embodiment of the invention, there is provided a heavy particle beam irradiation apparatus comprising: an ion source; and an ion beam accelerator that accelerates an ion beam from the ion source and outputs an accelerated ion beam as a heavy particle beam to irradiate a target site, wherein the ion source includes: a laser-ablation plasma generator that generates laser-ablation plasma from a target in a vacuum vessel, an ion beam extractor that generates the ion beam by extracting ions included in the laser-ablation plasma from the vacuum vessel, and an ion detector that detects unintended ions other than intended ions, which are obtained by ionizing elements of the target, out of ions in the vacuum vessel and that outputs a detection signal representing a value which is a number of the unintended ions or a mixing ratio of the unintended ions to the intended ions as a detection result, and wherein the heavy particle beam irradiation apparatus further comprises: an output-stopping gate valve that outputs the ion beam in response to an opening instructing signal and stops the output of the ion beam in response to a closing instructing signal, and an output-stop signal processing circuit that outputs the opening instructing signal to the output-stopping gate valve and outputs the closing instructing signal to the output-stopping gate valve when the value of the detection signal output from the ion detector is greater than a threshold value.

According to another embodiment of the invention, there is provided an ion source driving method comprising steps of generating laser-ablation plasma from a target in a vacuum vessel; generating an ion beam by extracting ions included in the laser-ablation plasma from the vacuum vessel; and causing an ion detector to detect unintended ions other than intended ions, which are obtained by ionizing elements of the target, out of ions in the vacuum vessel and to output a detection signal representing a value which is a number of the unintended ions or a mixing ratio of the unintended ions to the intended ions as a detection result.

According to another embodiment of the invention, there is provided a heavy particle beam irradiation method comprising steps of generating laser-ablation plasma from a target in a vacuum vessel; generating an ion beam by extracting ions included in the laser-ablation plasma from the vacuum vessel; accelerating the ion beam and outputting an accelerated ion beam as a heavy particle beam to irradiate a target site; causing an ion detector to detect unintended ions other than intended ions, which are obtained by ionizing elements of the target, out of ions in the vacuum vessel and to output a detection signal representing a value which is a number of the unintended ions or a mixing ratio of the unintended ions to the intended ions as a detection result; and stopping generation of the laser-ablation plasma when the value of the detection signal output from the ion detector is greater than a threshold value.

According to another embodiment of the invention, there is provided a heavy particle beam irradiation method comprising steps of generating laser-ablation plasma from a target in a vacuum vessel; generating an ion beam by extracting ions included in the laser-ablation plasma from the vacuum vessel; outputting the ion beam; accelerating the ion beam and outputting an accelerated ion beam as a heavy particle beam to irradiate a target site; causing an ion detector to detect unintended ions other than intended ions, which are obtained by ionizing elements of the target, out of ions in the vacuum vessel and to output a detection signal representing a value which is a number of the unintended ions or a mixing ratio of the unintended ions to the intended ions as a detection result; and stopping the output of the ion beam when the value of the detection signal output from the ion detector is greater than a threshold value.

According to an embodiment of the invention, it is possible to normally monitor unintended ions other than intended ions out of ions in a vacuum vessel.

Hereinafter, embodiments of an ion source according to the invention will be described with reference to the accompanying drawings. Elements equal or similar to each other are referenced by common reference numerals and description thereof is not repeated.

[First Embodiment]

FIG. 1 is a cross-sectional view schematically illustrating the configuration of an ion source 15 according to a first embodiment of the invention.

The ion source 15 according to the first embodiment includes a vacuum vessel 1, an ion detector 9, an ion beam extractor 18, and a laser-ablation plasma generator 27. The laser-ablation plasma generator 27 includes an irradiation device 13 and a high-voltage power supply 16.

The vacuum vessel 1 is formed of stainless steel, and a target 2 is disposed at the center of the vacuum vessel 1. For example, a carbon-based cylindrical or plate-like member can be used as the target 2. An exhaust port (not shown) is formed in the vacuum vessel 1. The exhaust port is connected to a vacuum pump (not shown) evacuating the vacuum vessel 1.

The high-voltage power supply 16 is connected to the target 2 in the vacuum vessel 1 via a power cable and applies a high voltage to the target 2.

An incident window 1a which a laser beam 3 to be described later enters is formed in the vacuum vessel 1. The irradiation device 13 irradiates the surface of the target 2 in the vacuum vessel 1 with the laser beam 3 via the incident window 1a from the outside of the vacuum vessel 1 to generate laser-ablation plasma 4.

The irradiation device 13 includes a laser power supply 13a, a laser oscillator 13b, and a plurality of laser mirrors 13c and 13d.

The laser power supply 13a is connected to the laser oscillator 13b via a power cable and supplies electric power to the laser oscillator 13b. The laser oscillator 13b generates a laser beam 3 using the electric power supplied from the laser power supply 13a. Examples of the laser beam 3 include a carbon gas laser or an Nd—YAG laser. The plurality of laser mirrors 13c and 13d concentrate the laser beam 3 by reflection and irradiates the surface of the target 2 in the vacuum vessel 1 via the incident window 1a from the outside of the vacuum vessel 1.

For example, when the plurality of laser mirrors employ the laser mirrors 13c and 13d shown in FIG. 1, the laser mirror 13c is disposed to reflect the laser beam 3 from the laser oscillator 13b to the laser mirror 13d, and the laser mirror 13d is disposed to irradiate the surface of the target 2 in the vacuum vessel 1 with the laser beam 3 from the laser mirror 13c via the incident window 1a from the outside of the vacuum vessel 1.

An ion extracting through-hole 1b disposed to face the surface of the target 2 in the vacuum vessel 1 is formed in the vacuum vessel 1. The ion beam extractor 18 generates an ion beam 5 by extracting ions included in the laser-ablation plasma 4 generated on the surface of the target 2 from the vacuum vessel 1 via the ion extracting through-hole 1b and outputs the generated ion beam to an external device 29.

The ion beam extractor 18 includes an extraction electrode 6, a plurality of intermediate electrodes 7a and 7b, an acceleration electrode 8, and a casing 17.

The extraction electrode 6 is disposed on the inner wall of the vacuum vessel 1 so as to face the surface of the target 2, and a through-hole is formed in the portion corresponding to the ion extracting through-hole 1b. A first bias voltage is applied to the extraction electrode 6, and the extraction electrode 6 extracts ions in the laser-ablation plasma 4 generated on the surface of the target 2 to itself by the use of the first bias voltage.

One end of the casing 17 is connected to the vacuum vessel 1 to cover the ion extracting through-hole 1b, and the other end thereof is connected to the external device 29. The intermediate electrodes 7a and 7b are disposed in the casing 17 to be parallel in the length direction of the casing 17 and to face each with a predetermined gap interposed therebetween. A second bias voltage lower than the first bias voltage is applied to the intermediate electrodes 7a and 7b, and the intermediate electrodes 7a and 7b extract the ions extracted to the extraction electrode 6 from the casing 17 by the use of the second bias voltage.

The acceleration electrode 8 is disposed at the other end of the casing 17 to face the extraction electrode 6. A third bias voltage (for example, a ground voltage) lower than the second bias voltage is applied to the acceleration electrode 8, and the acceleration electrode 8 accelerates the ions in the casing 17 by the use of the third bias voltage to generate an ion beam 5 and outputs the generated ion beam to the external device 29.

The ion detector 9 is disposed in the vacuum vessel 1. The ion detector 9 detects unintended ions other than intended ions ($C^{6+}$ ions), which are obtained by ionizing elements of the target 2, out of the ions in the vacuum vessel 1, and outputs a detection signal 14 representing a value, which is the number of unintended ions or the mixing ratio of the unintended ions to the intended ions, as the detection result via a signal cable from the vacuum vessel 1.

Examples of the ion detector 9 may include at least one of electric field and magnetic field, like a Q-mass (Q/MS) filter or Wien filter which detects analysis ions. The ion detector 9 also has an ion detecting sensor like an ion collector plate, a Faraday cup or a Micro channel plate. The electric field or the magnetic field is adjusted with respect to the ion detector 9 so as to detect unintended ions as the analysis ions. The ion detector 9 detects (analyzes) unintended ions by applying at least one of an electric field and a magnetic field to a portion (hereinafter, referred to as generation portion), which the laser-ablation plasma 4 is generated from, of the surface of the target 2 in the vacuum vessel 1, and outputs the detection signal 14 as the detection result from the vacuum vessel 1 via the signal cable.

Most of ions diffusing from the generation portion of the laser-ablation plasma 4 out of the ions generated by the laser-ablation plasma 4 are not extracted by the ion beam extractor 18 but stay in the vacuum vessel 1. On the other hand, the ions not diffusing from the generation portion of the laser-ablation plasma 4 are extracted by the ion beam extractor 18 disposed to face the surface of the target 2. Therefore, by disposing the ion detector 9 so as to apply at least one of an electric field and a magnetic field to the generation portion of the laser-ablation plasma 4, the ion detector 9 can detect ions extracted by the ion beam extractor 18.

Here, the unintended ions are not limited to one type. For example, when moisture or particles are attached to the target, ions of contaminants (such as hydrogen molecular ion ($H_2+$) and $O^{8+}$ ions) may be mixed as unintended ions in the vacuum vessel 1. When residual gas is present in the vacuum vessel 1, ions of residual gas components may be mixed as unintended ions in the vacuum vessel 1. In this way, a plurality of types of unintended ions such as ions of contaminants or ions of residual gas components are mixed in the vacuum vessel 1. Therefore, by disposing ion detectors 9 in the vacuum vessel 1 to correspond to a plurality of types of unintended ions, it may be possible to detect a plurality of types of unintended ions.

The operation (driving method) of the ion source 15 will be described below.

First, the high-voltage power supply 16 applies a high voltage to the target 2. The irradiation device 13 adjusts the energy and density of a laser beam 3 to generate $C^{6+}$ ions and irradiates the surface of the target 2 in the vacuum vessel 1 with the laser beam 3 to generate the laser-ablation plasma 4. At this time, the ion beam extractor 18 generates an ion beam 5 by extracting ions included in the laser-ablation plasma 4 from the vacuum vessel 1. The ion detector 9 detects unintended ions in the vacuum vessel 1 and outputs a detection signal 14 as the detection result to the outside of the vacuum vessel 1 via a signal cable.

As described above, in the ion source 15 according to the first embodiment, since the ion detector 9 detects the unintended ions in the vacuum vessel 1 and outputs the detection signal 14, it is possible to normally monitor the unintended ions without stopping the operation of the ion source 15.

In the ion source 15 according to the first embodiment, when the value of the detection signal 14 output from the ion detector 9 is greater than a threshold value, the number of unintended ions is not suitable for normal operation. Accordingly, it is possible to take a countermeasure of not extracting and outputting unintended ions other than intended ions as an ion beam from the vacuum vessel 1 with reference to the value of the detection value 14.

[Second Embodiment]

Only differences of an ion source according to a second embodiment of the invention from the first embodiment will be described below. The same elements as shown in FIG. 1 are referenced by the same reference numerals and elements not particularly described therein are the same as described in the first embodiment.

Figure 2:
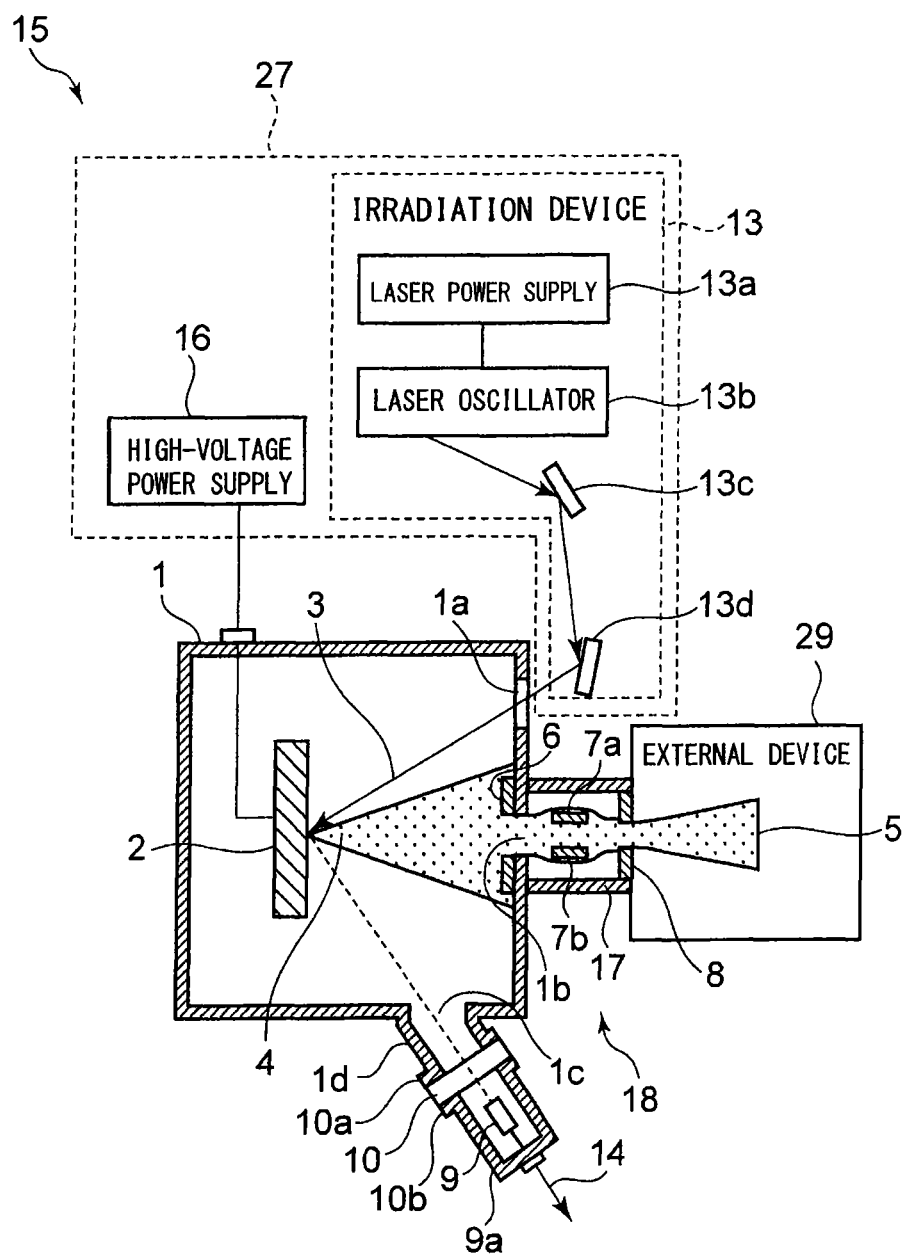
FIG. 2 is a cross-sectional view schematically illustrating the configuration of an ion source according to a second embodiment of the invention.

FIG. 2 is a cross-sectional view schematically illustrating the configuration of an ion source 15 according to the second embodiment.

The ion source 15 according to the second embodiment includes an ion detector housing 9a and an ion-detecting gate valve 10.

An ion detecting through-hole 1c used for the ion detector 9 to detect ions is formed in the vacuum vessel 1, and a nozzle id is disposed to cover the ion detecting through-hole 1c. A flange 10a is disposed at an end of the nozzle 1d.

The ion detector housing 9a is formed of, for example, stainless steel similarly to the vacuum vessel 1, and a flange 10b is formed at an end thereof. The ion-detecting gate valve 10 is interposed between the flange 10a and the flange 10b, and is able to be opened and closed. In a state where the ion-detecting gate valve 10 is opened, the ion detector housing 9a is evacuated along with the vacuum vessel 1. An ion detector 9 is housed in the ion detector housing 9a.

The ion detector 9 detects unintended ions by applying at least one of an electric field and a magnetic field to a portion, from which laser-ablation plasma 4, on the surface of the target 2 in the vacuum vessel 1, and outputs a detection signal 14 to the outside of the ion detector housing 9a via a signal cable as the detection result.

In the ion source 15 according to the second embodiment, since the ion detector 9 is disposed in the ion detector housing 9a connected to the vacuum vessel 1, the vacuum vessel 1 and the ion detector housing 9a can be separated from each other in a state where the ion-detecting gate value 10 is closed. That is, it is possible to attach and detach the ion detector housing 9a housing the ion detector 9 without stopping the operation of the ion source 15.

In the ion source 15 according to the second embodiment, maintenance of the ion detector 9 can be carried out when the ion detector housing 9a is detached. Accordingly, it is possible to improve maintenance performance of the ion detector 9.

[Third Embodiment]

Only differences of an ion source according to a third embodiment of the invention from the first and second embodiments will be described below. The same elements as shown in FIG. 1 are referenced by the same reference numerals and elements not particularly described therein are the same as described in the first and second embodiments.

Figure 3:
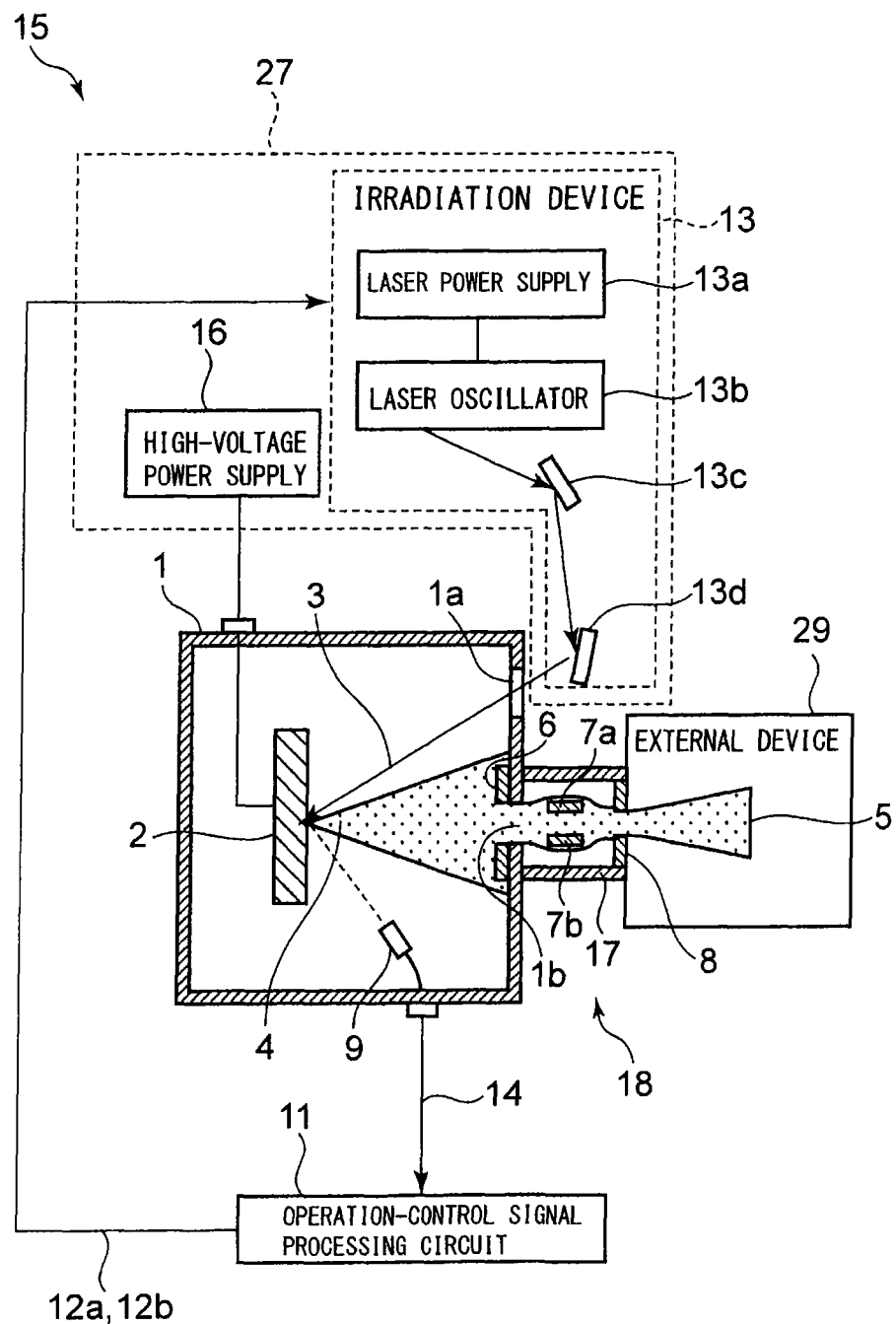
FIG. 3 is a cross-sectional view schematically illustrating the configuration of an ion source according to a third embodiment of the invention.

FIG. 3 is a cross-sectional view schematically illustrating the configuration of an ion source 15 according to the third embodiment.

The ion source 15 according to the third embodiment includes an operation-control signal processing circuit 11. The operation-control signal processing circuit 11 is connected to an ion detector 9 and an irradiation device 13 via signal cables. The irradiation device 13 irradiates the surface of a target 2 in a vacuum vessel 1 with a laser beam 3 from the outside the vacuum vessel 1 via an incident window 1a to generate laser-ablation plasma 4 in response to an operation instructing signal 12a. The irradiation device 13 stops the irradiation with the laser beam 3 in response to a stop instructing signal 12b. The operation-control signal processing circuit 11 outputs the operation instructing signal 12a to the irradiation device 13 and outputs the stop instructing signal 12b to the irradiation device 13 when the value of a detection signal 14 output from the ion detector 9 is greater than a threshold value.

Figure 4:
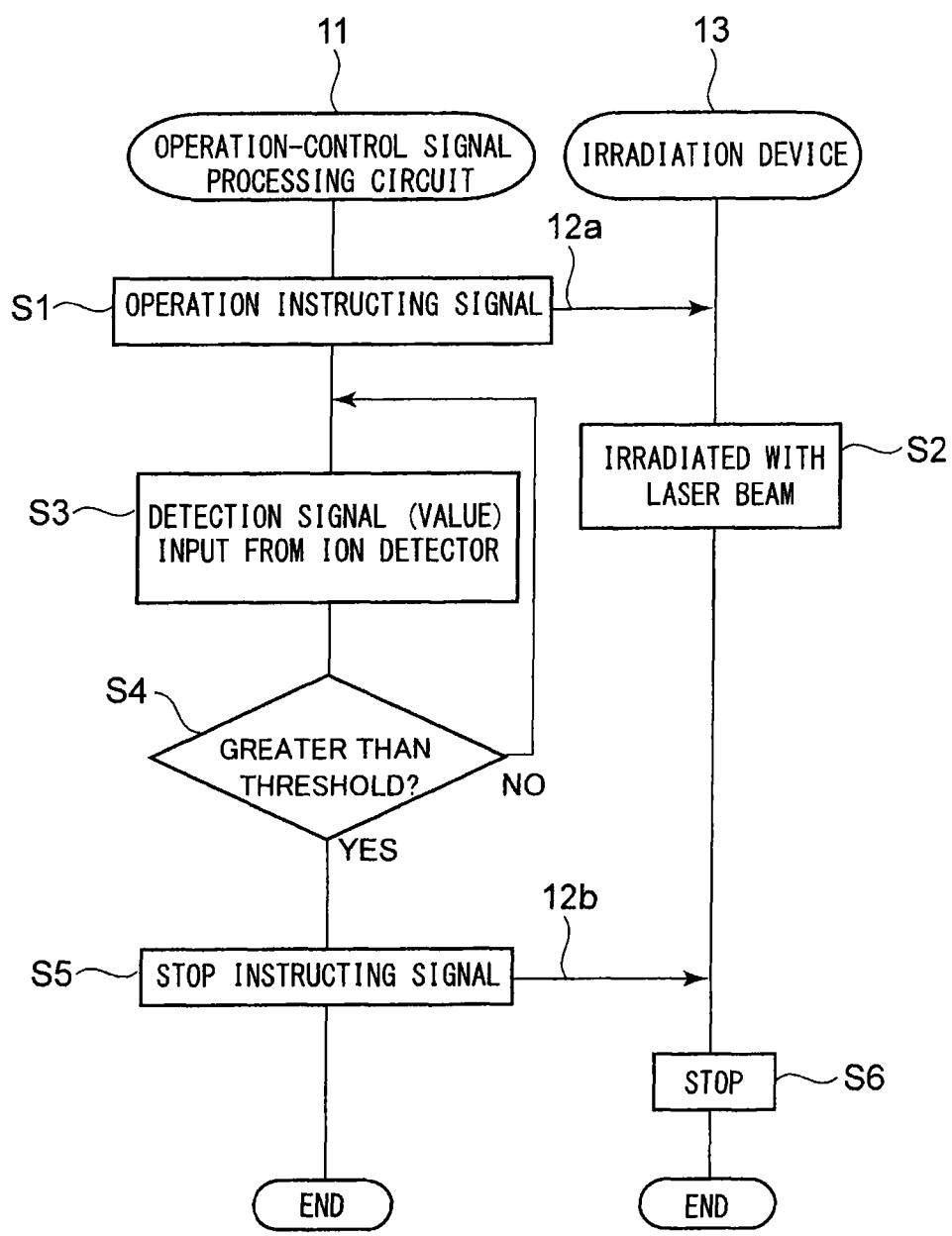
FIG. 4 is a flowchart illustrating the operation of the ion source shown in FIG. 3.

FIG. 4 is a flowchart illustrating the operation of the ion source 15 shown in FIG. 3.

First, a high-voltage power supply 16 supplies a high voltage to the target 2. A laser power supply 13a of the irradiation device 13 supplies electric power to a laser oscillator 13b. The operation-control signal processing circuit 11 outputs the operation instructing signal 12a to the laser oscillator 13b of the irradiation device 13 (step S1).

The laser oscillator 13b generates a laser beam 3 by the use of electric power supplied from the laser power supply 13a in response to the operation instructing signal 12a. A plurality of laser mirrors 13c and 13d concentrate the laser beam 3 by reflection, and irradiates the surface of the target 2 in the vacuum vessel 1 with the laser beam via the incident window 1a from the outside of the vacuum vessel 1. That is, the irradiation device 13 irradiates the surface of the target 2 in the vacuum vessel 1 with the laser beam 3 to generate the laser-ablation plasma 4 in response to the operation instructing signal 12a (step S2).

At this time, an ion beam extractor 18 generates an ion beam 5 by extracting ions included in the laser-ablation plasma 4 from the inside of the vacuum vessel 1, and outputs the generated ion beam to an external device 29.

The operation-control signal processing circuit 11 receives the detection signal 14 output from the ion detector 9 (step S3), and compares the value of the detection signal 14 with a threshold value (step S4).

When the value of the detection signal 14 is not greater than the threshold value (NO in step S4), the operation-control signal processing circuit 11 receives the next detection signal 14, and performs the processes of step S3 and subsequent steps thereof.

When the value of the detection signal 14 is greater than the threshold value (YES in step S4), the operation-control signal processing circuit 11 outputs the stop instructing signal 12b to the laser oscillator 13b of the irradiation device 13 (step S5).

The laser oscillator 13b stops the generation of the laser beam 3 in response to the stop instructing signal 12b. That is, the irradiation device 13 stops the irradiation with the laser beam 3 in response to the stop instructing signal 12b (step S6).

The operation-control signal processing circuit 11 outputs the operation instructing signal 12a and the stop instructing signal 12b to the laser oscillator 13b of the irradiation device 13, but may output the signals to the laser power supply 13a of the irradiation device 13. Alternatively, the operation-control signal processing circuit 11 may output the operation instructing signal 12a and the stop instructing signal 12b to at least one of the laser power supply 13a and the laser oscillator 13b of the irradiation device 13.

When the operation-control signal processing circuit 11 outputs the operation instructing signal 12a to the laser power supply 13a, the operation-control signal processing circuit 11 outputs the operation instructing signal 12a to the laser power supply 13a of the irradiation device 13 in step S1, and the laser power supply 13a supplies electric power to the laser oscillator 13b in response to the operation instructing signal 12a in step S2. Similarly, the operation-control signal processing circuit 11 outputs the stop instructing signal 12b to the laser power supply 13a of the irradiation device 13 in step S5 and the laser power supply 13a stops the supply of electric power to the laser oscillator 13b in response to the stop instructing signal 12b in step S6.

As described above, in the ion source 15 according to the third embodiment, since the operation-control signal processing circuit 11 stops the operation of the irradiation device 13 when the value of the detection signal 14 output from the ion detector 9 is greater than the threshold value. Accordingly, it is possible to prevent unintended ions other than intended ions from being extracted from the vacuum vessel 1 and being output as an ion beam 5.

[Fourth Embodiment]

Only differences of an ion source according to a fourth embodiment of the invention from the third embodiment will be described below. The same elements as shown in FIGS. 1 and 3 are referenced by the same reference numerals and elements not particularly described therein are the same as described in the third embodiment.

Figure 5:
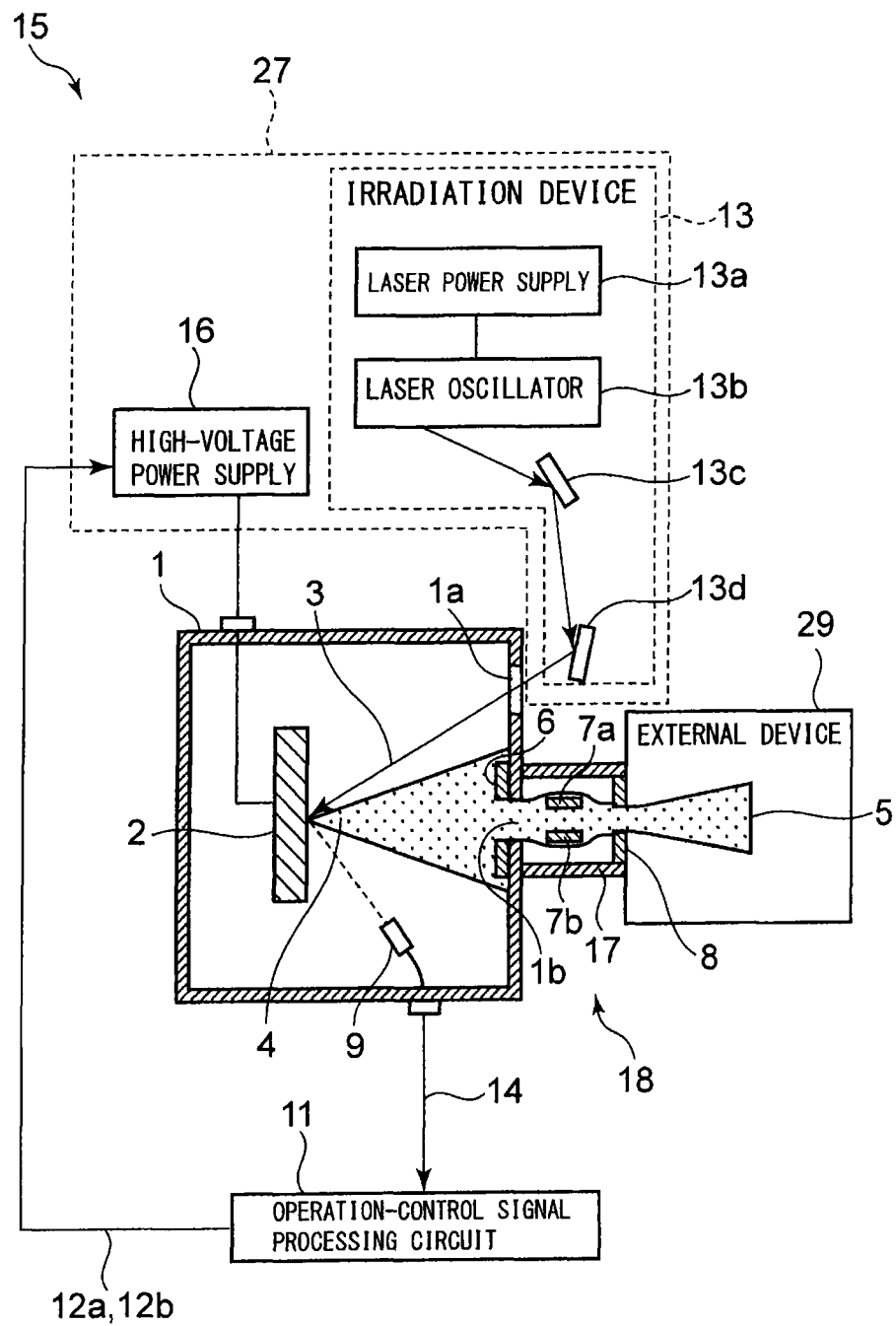
FIG. 5 is a cross-sectional view schematically illustrating the configuration of an ion source according to a fourth embodiment of the invention.

FIG. 5 is a cross-sectional view schematically illustrating the configuration of an ion source 15 according to the fourth embodiment of the invention.

An operation-control signal processing circuit 11 is connected to a high-voltage power supply 16 instead of the irradiation device 13 via a signal cable. The high-voltage power supply 16 supplies a high voltage to a target 2 in response to an operation instructing signal 12a and stops the supply of the voltage to the target 2 in response to a stop instructing signal 12b. The operation-control signal processing circuit 11 outputs the operation instructing signal 12a to the high-voltage power supply 16 and outputs the stop instructing signal 12b to the high-voltage power supply 16 when the value of a detection signal 14 output from an ion detector 9 is greater than a threshold value.

Figure 6:
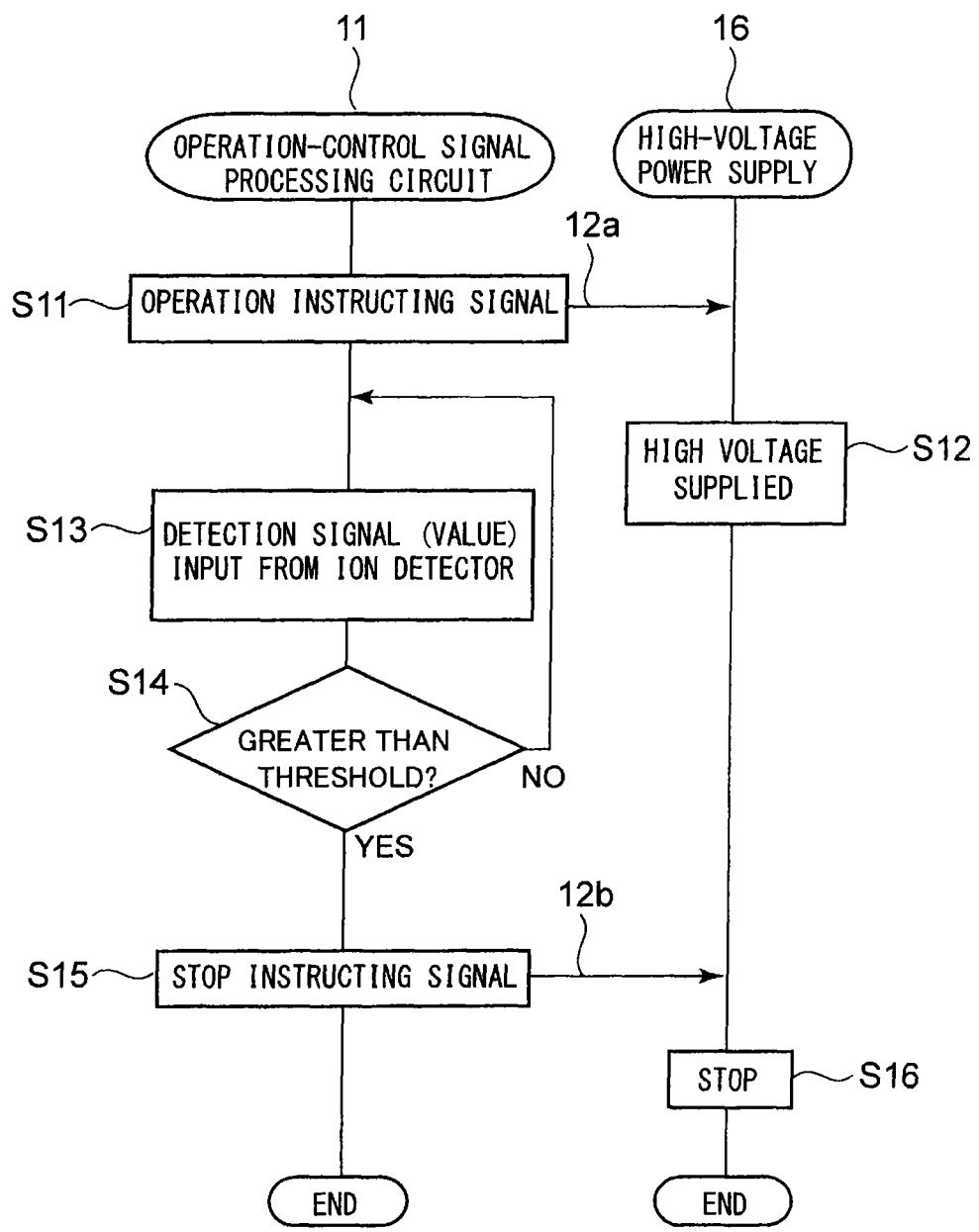
FIG. 6 is a flowchart illustrating the operation of the ion source shown in FIG. 5.

FIG. 6 is a flowchart illustrating the operation of the ion source 15 shown in FIG. 5.

First, the operation-control signal processing circuit 11 outputs the operation instructing signal 12a to the high-voltage power supply 16 (step S11).

The high-voltage power supply 16 supplies a high voltage to the target 2 in response to the operation instructing signal 12a (step S12).

At this time, the irradiation device 13 irradiates the surface of the target 2 in the vacuum vessel 1 with a laser beam 3 to generate laser-ablation plasma 4. The ion beam extractor 18 generates an ion beam 5 by extracting ions included in the laser-ablation plasma 4 from the inside the vacuum vessel 1 and outputs the generated ion beam to an external device 29.

The operation-control signal processing circuit 11 receives the detection signal 14 output from the ion detector 9 (step S13), and outputs the stop instructing signal 12b to the high-voltage power supply 16 when the value of the detection signal 14 is greater than the threshold value (YES in step S14) (step S15).

The high-voltage power supply 16 stops the supply of the voltage to the target 2 in response to the stop instructing signal 12b (step S16).

As described above, in the ion source 15 according to the fourth embodiment, the operation-control signal processing circuit 11 stops the operation of the high-voltage source 16 when the value of the detection signal 14 output from the ion detector 9 is greater than the threshold value. Accordingly, it is possible to prevent unintended ions other than intended ions from being extracted from the vacuum vessel 1 and being output as the ion beam 5.

Here, the operation-control signal processing circuit 11 may be connected to the ion detector 9, the irradiation device 13, and the high-voltage power supply 16 via signal cables. In this case, the flow of operations of the operation-control signal processing circuit 11 and the irradiation device 13 is the same as the flow of operations in the third embodiment shown in FIG. 4, and the flow of operations of the operation-control signal processing circuit 11 and the high-voltage power supply 16 is the same as the flow of operations in the fourth embodiment shown in FIG. 6.

The ion source 15 can be applied to a heavy particle beam irradiation apparatus. The heavy particle beam irradiation apparatus is used for cancer treatment and is an apparatus that accelerates an ion beam and irradiates a target site with the accelerated ion beam as a heavy particle beam. Therefore, when unintended ions other than intended ions ($C^{6+}$ ions) are included in the heavy particle beam, erroneous irradiation may be caused and is not desirable for an irradiation target. In the following application examples, the erroneous irradiation with a heavy particle beam is prevented.

FIRST APPLICATION EXAMPLE

Only differences of an application example of the ion source 15 from the above-mentioned embodiments will be described below. Elements not particularly described therein are the same as described in the above-mentioned embodiments.

Figure 7:
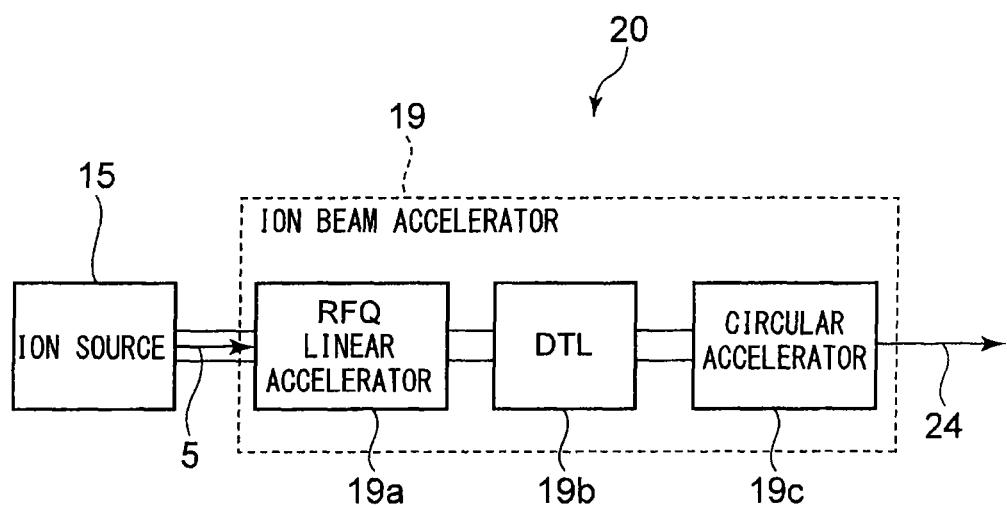
FIG. 7 is a block diagram illustrating the configuration of a heavy particle beam irradiation apparatus employing the ion source according to the third embodiment as a first application example.

FIG. 7 is a block diagram illustrating the configuration of a heavy particle beam irradiation apparatus 20 employing the ion source 15 according to the third embodiment as a first application example.

The heavy particle beam irradiation apparatus 20 according to the first application example includes an ion source 15 and an ion beam accelerator 19 which is the above-mentioned external device 29. The ion source 15 is the ion source 15 according to the third embodiment (see FIGS. 3 and 4). The ion beam accelerator 19 accelerates the ion beam 5 from the ion source 15 and outputs a heavy particle beam 24.

The ion beam accelerator 19 includes a radio frequency quadrupole (RFQ) linear accelerator 19a, a drift tube linear accelerator (DTL) 19b, and a circular accelerator 19c.

The RFQ linear accelerator 19a includes four electrodes (not shown) that are connected to the output of the ion source 15 and that form a quadrupole electric field by the use of RF waves. The RFQ linear accelerator 19a simultaneously accelerates and concentrates the ion beam 5 from the ion beam extractor 18 of the ion source 15 by the use of the quadrupole electric field.

The DTL 19b is connected to the output of the RFQ linear accelerator 19a. The DTL 19b includes electrodes (not shown) that form an electric field along the central axis by the use of RF waves, and a drift tube (not shown) that are separated from each other along the central axis. The DTL 19b accelerates the ion beam 5 step by step by accelerating the ion beam 5 from the RFQ linear accelerator 19a in a period of time in which the electric field is directed forward to the traveling direction parallel to the central axis, and transmitting the ion beam 5 through the drift tubes in a period of time in which the electric field is directed backward to the traveling direction.

The circular accelerator 19c is connected to the output of the DTL 19b. The circular accelerator 19c includes electrodes (not shown) that form an electric field along a peripheral orbit by the use of RF waves. The circular accelerator 19c peripherally accelerates the ion beam 5 from the DTL 19b along the peripheral orbit by the use of the electric field and outputs the accelerated ion beam as a heavy particle beam 24 to irradiate a target site.

The flow of operations of the heavy particle beam irradiation apparatus 20 according to the first application example will be described below.

In the ion source 15, the high-voltage power supply 16 supplies a high voltage to the target 2 (see FIG. 3) and the operation-control signal processing circuit 11 outputs the operation instructing signal 12a to the irradiation device 13 (see FIG. 3 and step S1 of FIG. 4). The irradiation device 13 irradiates the surface of the target 2 in the vacuum vessel 1 with the laser beam 3 to generate the laser-ablation plasma 4 in response to the operation instructing signal 12a (see FIG. 3 and step S2 of FIG. 4).

At this time, the ion beam extractor 18 of the ion source 15 generates an ion beam 5 by extracting ions included in the laser-ablation plasma 4 from the vacuum vessel 1 (see FIG. 3) and outputs the generated ion beam to the ion beam accelerator 19. The ion beam accelerator 19 accelerates the ion beam 5 from the ion source 15 and outputs the accelerated ion beam as the heavy particle beam 24.

When the value of the detection signal 14 output from the ion detector 9 of the ion source 15 is greater than the threshold value, the operation-control signal processing circuit 11 of the ion source 15 outputs the stop instructing signal 12b to the irradiation device 13 (see FIG. 3 and steps S3 to S5 of FIG. 4). The irradiation device 13 stops the generation of the laser beam 3 in response to the stop instructing signal 12b (see FIG. 3 and step S6 of FIG. 4).

As described above, in the heavy particle beam irradiation apparatus 20 according to the first application example, by employing the ion source 15 according to the third embodiment, the operation-control signal processing circuit 11 stops the operation of the laser-ablation plasma generator 27 (the irradiation device 13 in this case) when the value of the detection signal 14 output from the ion detector 9 is greater than the threshold value. Accordingly, it is possible to prevent unintended ions other than intended ions from being extracted from the vacuum vessel 1 and being output as an ion beam 5. That is, it is possible to prevent erroneous irradiation with the heavy particle beam 24.

The heavy particle beam irradiation apparatus 20 according to the first application example employs the ion source 15 according to the third embodiment, but is not limited to the third embodiment. For example, the ion source 15 according to the fourth embodiment (see FIGS. 5 and 6) may be employed.

When the ion source 15 according to the fourth embodiment is employed, the ion source 15 outputs the operation instructing signal 12a from the operation-control signal processing circuit 11 to the high-voltage power supply 16 (see FIG. 5 and step S11 of FIG. 6). The high-voltage power supply 16 supplies a high voltage to the target 2 in response to the operation instructing signal 12a (see FIG. 5 and step S12 of FIG. 6).

At this time, the irradiation device 13 of the ion source 15 irradiates the surface of the target 2 in the vacuum vessel 1 with the laser beam 3 to generate the laser-ablation plasma 4 (see FIG. 5). The ion beam extractor 18 of the ion source 15 generates the ion beam 5 by extracting the ions included in the laser-ablation plasma 4 from the vacuum vessel 1 (see FIG. 5) and outputs the generated ion beam to the ion beam accelerator 19. The ion beam accelerator 19 accelerates the ion beam 5 from the ion source 15 and outputs the accelerated ion beam as the heavy particle beam 24.

When the value of the detection signal 14 output from the ion detector 9 is greater than the threshold value, the operation-control signal processing circuit 11 of the ion source 15 outputs the stop instructing signal 12b to the high-voltage power supply 16 (see FIG. 5 and steps S13 to S15 of FIG. 6). The high-voltage power supply 16 stops the supply of the voltage to the target 2 in response to the stop instructing signal 12b (see FIG. 5 and step S16 of FIG. 6).

In the heavy particle beam irradiation apparatus 20 according to the first application example, by employing the ion source 15 according to the fourth embodiment, the operation-control signal processing circuit 11 stops the operation of the laser-ablation plasma generator 27 (the high-voltage power supply 16 in this case) when the value of the detection signal 14 output from the ion detector 9 is greater than the threshold value. Accordingly, it is possible to prevent erroneous irradiation with the heavy particle beam 24.

SECOND APPLICATION EXAMPLE

Only differences of an application example of the ion source 15 from the first application example will be described below. The same elements as shown in FIG. 7 are referenced by the same reference numerals, and elements not particularly described therein are the same as described in the first application example.

Figure 8:
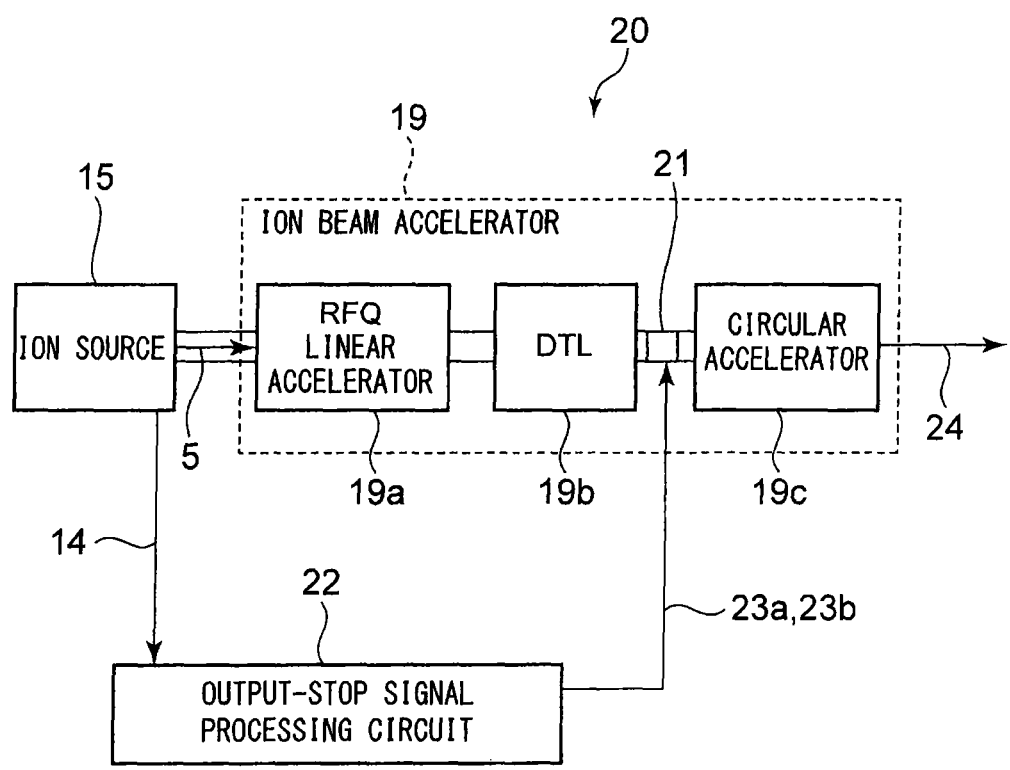
FIG. 8 is a block diagram illustrating the configuration of a heavy particle beam irradiation apparatus employing the ion source according to the first embodiment as a second application example.

FIG. 8 is a block diagram illustrating the configuration of a heavy particle beam irradiation apparatus 20 employing the ion source 15 according to the first embodiment as a second application example.

The heavy particle beam irradiation apparatus 20 according to the second application example includes the ion source 15 (see FIG. 1) according to the first embodiment, an ion beam accelerator 19, and an output-stopping gate valve 21.

The output-stopping gate valve 21 is installed in any one of the input (the output of the ion source 15) of the RFQ linear accelerator 19a of the ion beam accelerator 19, the input of the DTL 19b, and the input of the circular accelerator 19c. In FIG. 8, the output-stopping gate valve 21 is disposed between the output of the DTL 19b of the ion beam accelerator 19 and the input of the circular accelerator 19c. The output-stopping gate valve 21 is opened to output an ion beam 5 in response to an opening instructing signal 23a, and is closed to stop the output of the ion beam 5 in response to a closing instructing signal 23b.

An output-stopping signal processing circuit 22 is connected to the ion detector 9 and the output-stopping gate valve 21 via signal cables. The output-stopping signal processing circuit 22 outputs the opening instructing signal 23a to the output-stopping gate valve 21, and outputs the closing instructing signal 23b to the output-stopping gate valve 21 when the value of the detection signal 14 output from the ion detector 9 is greater than the threshold value.

Figure 9:
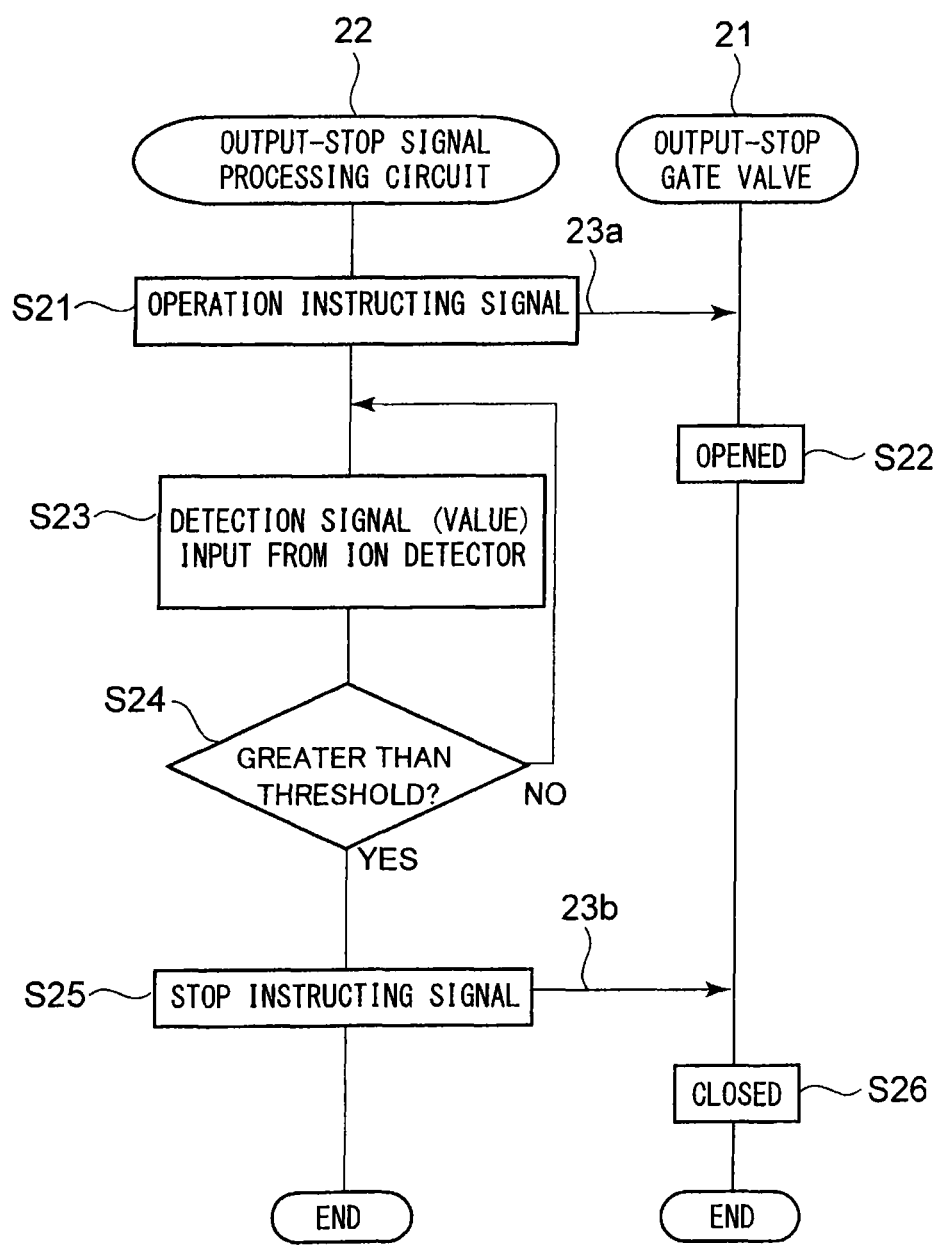
FIG. 9 is a flowchart illustrating the operation of the heavy particle beam irradiation apparatus shown in FIG. 8.

FIG. 9 is a flowchart illustrating the operation of the heavy particle beam irradiation apparatus 20 shown in FIG. 8.

First, the output-stopping signal processing circuit 22 outputs the opening instructing signal 23a to the output-stopping gate valve 21 (step S21). The output-stopping gate valve 21 is opened in response to the opening instructing signal 23a (step S22).

In the ion source 15, the laser-ablation plasma generator 27 (the irradiation device 13 and the high-voltage power supply 16) generates the laser-ablation plasma 4 from the surface of the target 2 in the vacuum vessel 1 (see FIG. 1), and the ion beam extractor 18 generates the ion beam 5 by extracting the ions included in the laser-ablation plasma 4 from the vacuum vessel 1 (see FIG. 1) and outputs the generated ion beam to the RFQ linear accelerator 19a. The RFQ linear accelerator 19a accelerates and concentrates the ion beam 5 from the ion beam extractor 18 of the ion source 15, and the DTL 19b accelerates the ion beam 5 step by step. Here, since the output-stopping gate valve 21 is opened, the ion beam 5 is output from the DTL 19b to the circular accelerator 19c. The circular accelerator 19c peripherally accelerates the ion beam 5 from the DTL 19b and outputs the accelerated ion beam as the heavy particle beam 24.

The output-stopping signal processing circuit 22 receives the detection signal 14 output from the ion detector 9 (step S23), and compares the value of the detection signal 14 with a threshold value (step S24).

When the value of the detection signal 14 is not greater than the threshold value (NO in step S24), the number of unintended ions other than intended ions ($C^{6+}$ ions) is small. In this case, the output-stopping signal processing circuit 22 receives the next detection signal 14 and performs the processes of step S23 and subsequent steps thereof.

When the value of the detection signal 14 is greater than the threshold value (YES in step S24), the number of unintended ions is large. In this case, the output-stopping signal processing circuit 22 outputs the closing instructing signal 23b to the output-stopping gate valve 21 (step S25).

The output-stopping gate valve 21 is closed in response to the closing instructing signal 23b (step S26).

As described above, in the heavy particle beam irradiation apparatus 20 according to the second application example, the output-stopping signal processing circuit 22 closes the output-stopping gate valve 21 to stop the output of the ion beam 5 when the value of the detection signal 14 output from the ion detector 9 is greater than the threshold value. Accordingly, it is possible to prevent unintended ions other than intended ions from being extracted from the vacuum vessel 1 and being output as the ion beam 5. That is, it is possible to prevent erroneous irradiation with the heavy particle beam 24.

The heavy particle beam irradiation apparatus 20 according to the second application example employs the ion source 15 according to the first embodiment, but is not limited thereto. For example, the ion source 15 (see FIG. 2) according to the second embodiment may be employed. In the heavy particle beam irradiation apparatus 20 according to the second application example, by employing the ion source 15 according to the second embodiment, the output-stopping signal processing circuit 22 closes the output-stopping gate valve 21 to stop the output of the ion beam 5 when the value of the detection signal 14 output from the ion detector 9 is greater than the threshold value. Accordingly, it is possible to prevent erroneous irradiation with the heavy particle beam 24.

The heavy particle beam irradiation apparatus 20 according to the second application example may employ the ion source 15 according to the third embodiment (see FIGS. 3 and 4) or the ion source 15 according to the fourth embodiment (see FIGS. 5 and 6). In the heavy particle beam irradiation apparatus 20 according to the second application example employing the ion source 15 according to the third or fourth embodiment, when the value of the detection signal 14 output from the ion detector 9 is greater than the threshold value, the operation-control signal processing circuit 11 stops the operation of the laser-ablation plasma generator 27 (the irradiation device 13 or the high-voltage power supply 16) and the output-stopping signal processing circuit 22 closes the output-stopping gate valve 21 to stop the output of the ion beam 5. Accordingly, it is possible to further prevent erroneous irradiation of the heavy particle beam 24, compared with the case where the ion source 15 according to the first or second embodiment is employed.

In the heavy particle beam irradiation apparatus 20 according to the second application example employing the ion source 15 according to the third or fourth embodiment, the output-stopping signal processing circuit 22 may be disposed separately from the operation-control signal processing circuit 11 as described above, or may be unified with the operation-control signal processing circuit 11.

THIRD APPLICATION EXAMPLE

Only differences of an application example of the ion source 15 from the first application example will be described below. Elements not particularly described therein are the same as described in the first application example.

Figure 10:
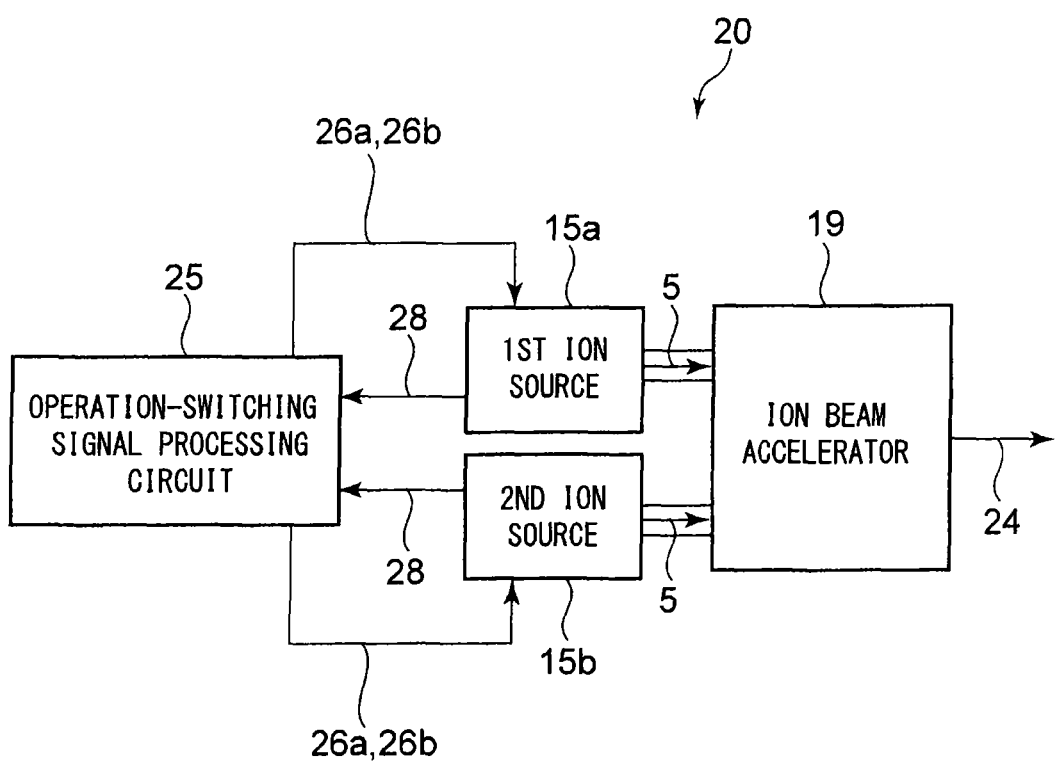
FIG. 10 is a block diagram illustrating the configuration of a heavy particle beam irradiation apparatus employing the ion source according to the third embodiment as a third application example.

FIG. 10 is a block diagram illustrating the configuration of a heavy particle beam irradiation apparatus 20 employing the ion source 15 according to the third embodiment as a third application example.

The heavy particle beam irradiation apparatus 20 includes a first ion source 15a, a second ion source 15b, an ion beam accelerator 19, and an operation-switching signal processing circuit 25. The first ion source 15a and the second ion source 15b are the same as the ion source 15 (see FIGS. 3 and 4) according to the third embodiment.

The operation-control signal processing circuit 11 of the first ion source 15a outputs the operation instructing signal 12a to the irradiation device 13 (see FIG. 3) of the first ion beam 15a in response to a first control signal 26a and outputs the stop instructing signal 12b to the irradiation device 13 of the first ion beam 15a in response to a second control signal 26b. Similarly, the operation-control signal processing circuit 11 of the second ion source 15b outputs the operation instructing signal 12a to the irradiation device 13 of the second ion beam 15b in response to the first control signal 26a and outputs the stop instructing signal 12b to the irradiation device 13 of the second ion source 15b in response to the second control signal 26b.

The operation-switching signal processing circuit 25 is connected to the operation-control signal processing circuits 11 of the first ion source 15a and the second ion source 15b via signal cables. The operation-switching signal processing circuit 25 controls the operation-control signal processing circuits 11 of the ion sources 15a and 15b by the use of the first control signal 26a and the second control signal 26b so as to switch the ion source to be operated to the first ion source 15a or the second ion source 15b. The ion beam accelerator 19 accelerates the ion beam 5 from the first ion beam 15a or the second ion beam 15b, and outputs the accelerated ion beam as the heavy particle beam 24 to irradiate a target site.

Figure 11:
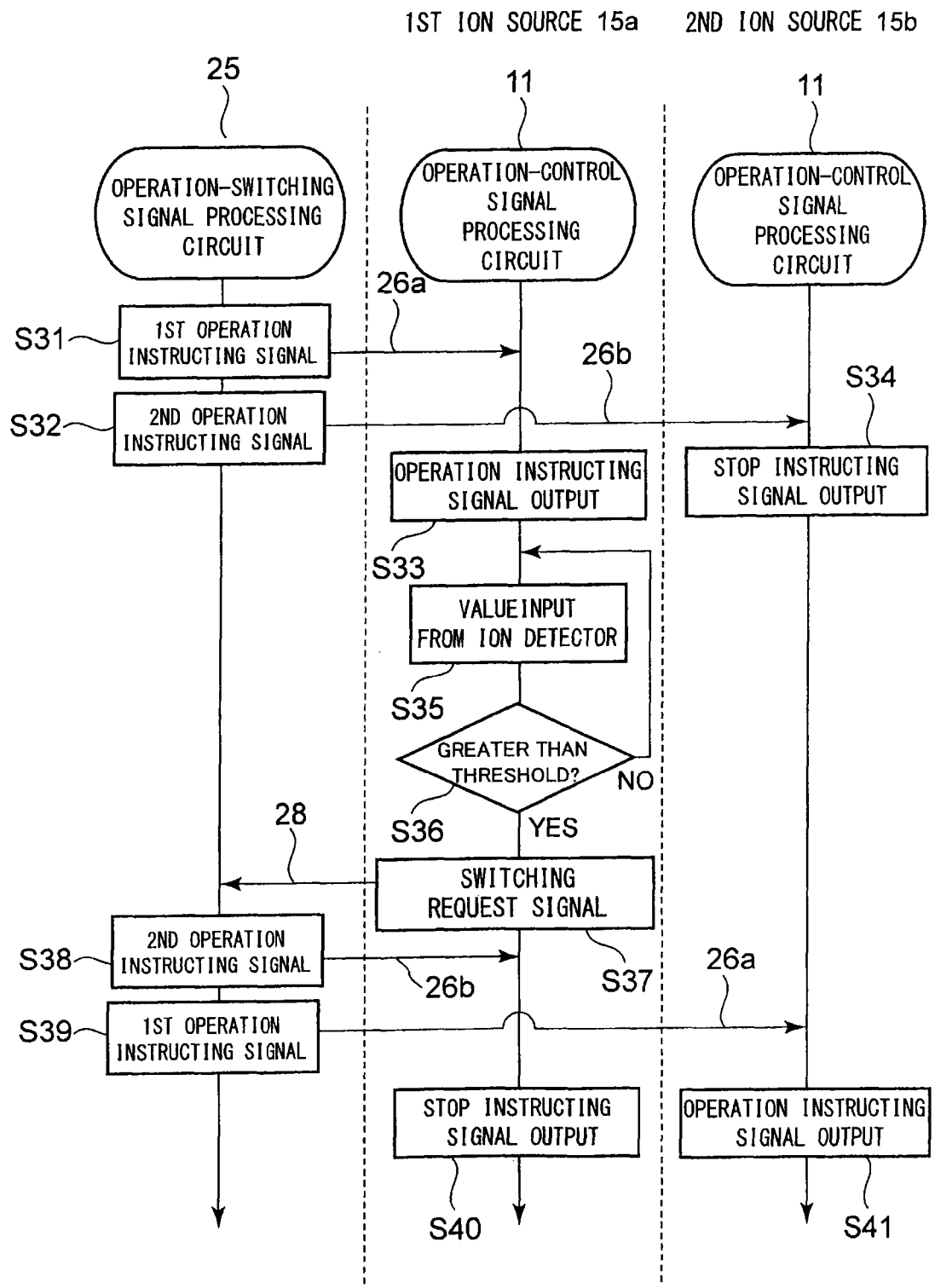
FIG. 11 is a flowchart illustrating the operation of the heavy particle beam irradiation apparatus shown in FIG. 10.

FIG. 11 is a flowchart illustrating the operation of the heavy particle beam irradiation apparatus 20 shown in FIG. 10.

An example where the first ion source 15a is operated and the operation of the second ion source 15b is stopped will be described below. The high-voltage power supplies 16 of the ion sources 15a and 15b supply a high voltage to the target 2 (see FIG. 3).

The operation-switching signal processing circuit 25 outputs the first control signal 26a to the operation-control signal processing circuit 11 of the first ion source 15a (step S31) and outputs the second control signal 26b to the operation-control signal processing circuit 11 of the second ion source 15b (step S32).

At this time, the operation-control signal processing circuit 11 of the first ion source 15a outputs the operation instructing signal 12a to the irradiation device 13 of the first ion source 15a in response to the first control signal 26a (step S33), and the operation-control signal processing circuit 11 of the second ion source 15b outputs the stop instructing signal 12b to the irradiation device 13 of the second ion source 15b in response to the second control signal 26b (step S34).

In step S33, the irradiation device 13 of the first ion source 15a irradiates the surface of the target 2 in the vacuum vessel 1 with a laser beam 3 to generate the laser-ablation plasma 4 in response to the operation instructing signal 12a (see FIG. 3 and step S2 of FIG. 4). The ion beam extractor 18 of the first ion source 15a generates an ion beam 5 by extracting ions included in the laser-ablation plasma 4 from the vacuum vessel 1 (see FIG. 3), and outputs the ion beam to the ion beam accelerator 19. The ion beam accelerator 19 accelerates the ion beam 5 from the ion source 15, and outputs the accelerated ion beam as the heavy particle beam 24.

The operation-control signal processing circuit 11 of the first ion source 15a receives the detection signal 14 output from the ion detector 9 of the first ion source 15a (step S35), and compares the value of the detection signal 14 with a threshold value (step S36).

When the value of the detection signal 14 is greater than the threshold value (YES in step S36), the operation-control signal processing circuit 11 of the first ion source 15a outputs a switching request signal 28 representing the comparison result to the operation-switching signal processing circuit 25 (step S37).

When receiving the switching request signal 28 from the operation-control signal processing circuit 11 of the first ion source 15a, the operation-switching signal processing circuit 25 recognizes that the value of the detection signal 14 output from the ion detector 9 of the first ion source 15a is greater than the threshold value, outputs the second control signal 26b to the operation-control signal processing circuit 11 of the first ion source 15a (step S38), and outputs the first control signal 26a to the operation-control signal processing circuit 11 of the second ion source 15b (step S39).

At this time, the operation-control signal processing circuit 11 of the first ion source 15a outputs the stop instructing signal 12b to the irradiation device 13 of the first ion source 15a in response to the second control signal 26b (step S40), and the operation-control signal processing circuit 11 of the second ion source 15b outputs the operation instructing signal 12a to the irradiation device 13 of the second ion source 15b in response to the first control signal 26a (step S41).

In step S40, the irradiation device 13 of the first ion source 15a stops the generation of the laser beam 3 in response to the stop instructing signal 12b. That is, the operation of the first ion source 15a is stopped (see FIG. 3 and step S6 of FIG. 4). In step S41, the irradiation device 13 of the second ion source 15b irradiates the surface of the target 2 in the vacuum vessel 1 with the laser beam 3 to generate the laser-ablation plasma 4 in response to the operation instructing signal 12a. That is, the second ion source 15b is operated (see FIG. 3 and step S2 of FIG. 4).

Thereafter, the first ion source 15a and the second ion source 15b are alternately operated.

As described above, in the heavy particle beam irradiation apparatus 20 according to the third application example, by employing the ion source 15 according to the third embodiment, the operation-switching signal processing circuit 25 switches the first ion source 15a to the second ion source 15b when the value of the detection signal 14 output from the ion detector 9 of the first ion source 15a is greater than the threshold value. Accordingly, it is possible to prevent unintended ions other than intended ions from being extracted from the vacuum vessel 1 and being output as the ion beam 5. That is, it is possible to prevent erroneous irradiation with the heavy particle beam 24.

In the heavy particle beam irradiation apparatus 20 according to the third application example, since the first ion source 15a and the second ion source 15b are alternately operated, it is possible to continue to irradiate the target site with the heavy particle beam 24.

The heavy particle beam irradiation apparatus 20 according to the third application example employs the ion source 15 according to the third embodiment, but is not limited thereto. For example, the ion source 15 according to the fourth embodiment (see FIGS. 5 and 6) may be employed. An example where the first ion source 15a is operated and the operation of the second ion source 15b is stopped when the ion source 15 according to the fourth embodiment is employed will be described below.

The operation-switching signal processing circuit 25 outputs the first control signal 26a to the operation-control signal processing circuit 11 of the first ion source 15a (step S31), and outputs the second control signal 26b to the operation-control signal processing circuit 11 of the second ion source 15b (step S32).

The operation-control signal processing circuit 11 of the first ion source 15a outputs the operation instructing signal 12a to the high-voltage power supply 16 of the first ion source 15a in response to the first control signal 26a (step S33), and the operation-control signal processing circuit 11 of the second ion source 15b outputs the stop instructing signal 12b to the high-voltage power supply 16 of the second ion source 15b in response to the second control signal 26b (step S34).

In step S33, the high-voltage power supply 16 of the first ion source 15a supplies a high voltage to the target 2 in response to the operation instructing signal 12a (see FIG. 5 and step S12 of FIG. 6). At this time, the irradiation device 13 of the first ion source 15a irradiates the surface of the target 2 in the vacuum vessel 1 with the laser beam 3 to generate the laser-ablation plasma 4 (see FIG. 5). The ion beam extractor 18 of the first ion source 15a generates an ion beam 5 by extracting ions included in the laser-ablation plasma 4 from the vacuum vessel 1 (see FIG. 5) and outputs the generated ion beam to the ion beam accelerator 19. The ion beam accelerator 19 accelerates the ion beam 5 from the ion source 15 and outputs the accelerated ion beam as the heavy particle beam 24.

When the value of the detection signal 14 output from the ion detector 9 of the first ion source 15a is greater than the threshold value, the operation-control signal processing circuit 11 of the first ion source 15a outputs the switching request signal 28 to the operation-switching signal processing circuit 25, and the operation-switching signal processing circuit 25 outputs the second control signal 26b to the operation-control signal processing circuit 11 of the first ion source 15a and outputs the first control signal 26a to the operation-control signal processing circuit 11 of the second ion source 15b in response to the switching request signal 28 (steps S35 to S39).

At this time, the operation-control signal processing circuit 11 of the first ion source 15a outputs the stop instructing signal 12b to the irradiation device 13 of the first ion source 15a in response to the second control signal 26b (step S40), and the operation-control signal processing circuit 11 of the second ion source 15b outputs the operation instructing signal 12a to the irradiation device 13 of the second ion source 15b in response to the first control signal 26a (step S41).

In step S40, the high-voltage power supply 16 of the first ion source 15a stops the supply of the voltage to the target 2 in response to the stop instructing signal 12b. That is, the operation of the first ion source 15a is stopped (see FIG. 5 and step S16 of FIG. 6). In step S41, the high-voltage power supply 16 of the second ion source 15b supplies a high voltage to the target 2 in response to the operation instructing signal 12a. That is, the second ion source 15b is operated (see FIG. 5 and step S12 of FIG. 6).

Thereafter, the first ion source 15a and the second ion source 15b are alternately operated.

In the heavy particle beam irradiation apparatus 20 according to the third application example employing the ion source 15 according to the fourth embodiment, the operation-switching signal processing circuit 25 switches the first ion source 15a to the second ion source 15b when the value of the detection signal 14 output from the ion detector 9 of the first ion source 15a is greater than the threshold value. Accordingly, it is possible to prevent erroneous irradiation with the heavy particle beam 24. When the ion source 15 according to the fourth embodiment is employed, the first ion source 15a and the second ion source 15b are alternately operated and it is thus possible to continue to irradiate the target site with the heavy particle beam 24.

[Other Embodiments]

While several embodiments of the invention have been described above, these embodiments are intended only for exemplification but are not intended for limiting the scope of the invention. These embodiments can be modified in various forms, and can be omitted, substituted, or combined in features thereof without departing from the concept of the invention. These embodiments or modifications belong to the scope or concept of the invention and belong to the invention described in the appended claims and the equivalent scope thereto.

What is claimed is:

1. An ion source comprising:
a laser-ablation plasma generator that generates laser-ablation plasma from a target in a vacuum vessel;

an ion beam extractor that generates an ion beam by extracting ions included in the laser-ablation plasma from the vacuum vessel to output the generated ion beam to an external device;

an ion detector that detects only unintended ions that are not extracted through the ion beam extractor, the unintended ions having diverged from a line from the target to the ion beam extractor, the unintended ions being obtained by ionizing elements of the target, out of ions in the vacuum vessel, the ion detector outputting a detection signal representing a value which is a number of the unintended ions or a mixing ratio of the unintended ions to the intended ions as a detection result, wherein the ion detector is disposed at a position diverged from the line from the target to the ion beam extractor so as not to interfere with the ion beam generated by the ion beam extractor and output to the external device; and an operating-control signal processing circuit that outputs an operation instructing signal to the laser-ablation plasma generator and outputs a stop instructing signal to the laser-ablation plasma generator when the value of the detection signal output from the ion detector is greater than a threshold value, wherein the laser-ablation plasma generator generates the laser-ablation plasma in response to the operation instructing signal and stops generation of the laser-ablation plasma in response to the stop instructing signal.

2. The ion source according to claim 1, wherein the ion detector detects the unintended ions by applying at least one of an electric field and a magnetic field to a portion on a surface of the target from which the laser-ablation plasma is generated and outputs the detection signal as the detection result.

3. The ion source according to claim 1, further comprising:
an ion detector housing that is connected to the vacuum vessel and that houses the ion detector; and
an ion-detecting gate valve that is disposed between the vacuum vessel and the ion detector housing and that is able to be opened and closed.

4. The ion source according to claim 1, wherein the laser-ablation plasma generator includes an irradiation device that irradiates a surface of the target in the vacuum vessel with a laser beam in response to the operation instructing signal to generate the laser-ablation plasma and stops irradiation with the laser beam in response to the stop instructing signal, and
wherein the operation-control signal processing circuit outputs the operation instructing signal to the irradiation device and outputs the stop instructing signal to the irradiation device when the value of the detection signal output from the ion detector is greater than the threshold value.

5. The ion source according to claim 4, wherein the irradiation device includes
a laser power supply that supplies electric power,
a laser oscillator that generates the laser beam by the use of the electric power supplied from the laser power supply, and
a plurality of laser mirrors that concentrate the laser beam by reflection and irradiate the surface of the target in the vacuum vessel with the concentrated laser beam, and
wherein the operation-control signal processing circuit outputs the operation instructing signal to at least one of the laser power supply and the laser oscillator of the irradiation device and outputs the stop instructing signal to the at least one of t the laser power supply and the laser oscillator of the irradiation device when the value of the detection signal output from the ion detector is greater than the threshold value.

6. The ion source according to claim 1, wherein the laser-ablation plasma generator includes a high-voltage power supply that supplies a voltage to the target in the vacuum vessel in response to the operation instructing signal and stops supply of the voltage to the target in response to the stop instructing signal,
wherein the operation-control signal processing circuit outputs the operation instructing signal to the high-voltage power supply and outputs the stop instructing signal to the high-voltage power supply when the value of the detection signal output from the ion detector is greater than the threshold value.

7. A heavy particle beam irradiation apparatus comprising:
at least one ion source; and
an ion beam accelerator that accelerates an ion beam from the at least one ion source and outputs an accelerated ion beam as a heavy particle beam to irradiate a target site,
wherein the at least one ion source each includes:
a laser-ablation plasma generator that generates laser-ablation plasma from a target in a vacuum vessel in response to an operation instructing signal and stops the generation of the laser-ablation plasma in response to a stop instructing signal,
an ion beam extractor that generates an ion beam by extracting ions included in the laser-ablation plasma from the vacuum vessel to output the generated ion beam to an external device;
an ion detector that detects only unintended ions that are not extracted through the ion beam extractor, the unintended ions having diverged from a line from the target to the ion beam extractor, the unintended ions being obtained by ionizing elements of the target, out of the ions in the vacuum vessel, the ion detector outputting a detection signal representing a value, which is a number of the unintended ions or a mixing ratio of the unintended ions to the intended ions, as a detection result, wherein the ion detector is disposed at a position diverged from the line from the target to the ion beam extractor so as not to interfere with the ion beam generated by the ion beam extractor and output to the external device, and
an operation-control signal processing circuit that outputs the operation instructing signal to the at least one laser-ablation plasma generator and outputs the stop instructing signal to the at least one laser-ablation plasma generator when the value of the detection signal output from the ion detector is greater than a threshold value,
wherein the laser-ablation plasma generator generates the laser-ablation plasma in response to the operation instructing signal and stops generation of the laser-ablation plasma in response to the stop instructing signal.

8. The heavy particle beam irradiation apparatus according to claim 7, wherein
the at least one ion source includes first and second ion sources, and
the heavy particle beam irradiation apparatus further comprises an operation-switching signal processing circuit that controls the operation-control signal processing circuits of the first and second ion sources to switch the ion sources to selectively operate one of the first and second ion sources.

9. The heavy particle beam irradiation apparatus according to claim 8, wherein the operation-control signal processing circuits of the first and second ion sources output the operation instructing signal to the laser-ablation plasma generator in response to a first control signal and outputs the stop instructing signal to the laser-ablation plasma generator in response to a second control signal, wherein the operation-switching signal processing circuit:
outputs the first control signal to the operation-control signal processing circuit of the first ion source and outputs the second control signal to the operation-control signal processing circuit of the second ion source, and
outputs the second control signal to the operation-control signal processing circuit of the first ion source and outputs the first control signal to the operation-control signal processing circuit of the second ion source, when the value of the detection signal output from the ion detector of the first ion source is greater than the threshold value.

10. A heavy particle beam irradiation apparatus comprising:
an ion source; and
an ion beam accelerator that accelerates an ion beam from the ion source and outputs an accelerated ion beam as a heavy particle beam to irradiate a target site,
wherein the ion source includes:
a laser-ablation plasma generator that generates laser-ablation plasma from a target in a vacuum vessel,
an ion beam extractor that generates an ion beam by extracting ions included in the laser-ablation plasma from the vacuum vessel to output the generated ion beam to an external device;
an ion detector that detects only unintended ions that are not extracted through the ion beam extractor, the unintended ions having diverged from a line from the target to the ion beam extractor, the unintended ions being obtained by ionizing elements of the target, out of ions in the vacuum vessel, the ion detector outputting a detection signal representing a value which is a number of the unintended ions or a mixing ratio of the unintended ions to the intended ions as a detection result, wherein the ion detector is disposed at a position diverged from the line from the target to the ion beam extractor so as not to interfere with the ion beam generated by the ion beam extractor and output to the external device, and
wherein the heavy particle beam irradiation apparatus further comprises:
an output-stopping gate valve that outputs the ion beam in response to an opening instructing signal and stops the output of the ion beam in response to a closing instructing signal, and
an output-stop signal processing circuit that outputs the opening instructing signal to the output-stopping gate valve and outputs the closing instructing signal to the output-stopping gate valve when the value of the detection signal output from the ion detector is greater than a threshold value.

11. An ion source driving method comprising:
generating laser-ablation plasma from a target in a vacuum vessel;
generating, by an ion beam extractor, an ion beam by extracting ions included in the laser-ablation plasma from the vacuum vessel;
causing an ion detector to detect only unintended ions that are not extracted through the ion beam extractor, the unintended ions having diverged from a line from the target to the ion beam extractor, the unintended ions being obtained by ionizing elements of the target, out of ions in the vacuum vessel and to output a detection signal representing a value which is a number of the unintended ions or a mixing ratio of the unintended ions to the intended ions as a detection result, wherein the ion detector is disposed at a position diverged from the line from the target to the ion beam extractor so as not to interfere with the generated ion beam output to the external device; and
stopping generation of the laser-ablation plasma when the value of the detection signal output from the ion detector is greater than a threshold value.

12. A heavy particle beam irradiation method comprising:
generating laser-ablation plasma from a target in a vacuum vessel;
generating, by an ion beam extractor, an ion beam by extracting ions included in the laser-ablation plasma from the vacuum vessel;
accelerating the ion beam and outputting an accelerated ion beam as a heavy particle beam to irradiate a target site;
causing an ion detector to detect only unintended ions that are not extracted through the ion beam extractor, the unintended ions having diverged from a line from the target to the ion beam extractor, the unintended ions being obtained by ionizing elements of the target, out of ions in the vacuum vessel, the ion detector outputting a detection signal representing a value which is a number of the unintended ions or a mixing ratio of the unintended ions to the intended ions as a detection result, wherein the ion detector is disposed at a position diverged from the line from the target to the ion beam extractor so as not to interfere with the generated ion beam output to the external device; and
stopping generation of the laser-ablation plasma when the value of the detection signal output from the ion detector is greater than a threshold value.

13. A heavy particle beam irradiation method comprising:
generating laser-ablation plasma from a target in a vacuum vessel;
generating, by an ion beam extractor, an ion beam by extracting ions included in the laser-ablation plasma from the vacuum vessel;
outputting the ion beam;
accelerating the ion beam and outputting an accelerated ion beam as a heavy particle beam to irradiate a target site;
causing an ion detector to detect only unintended ions that are not extracted through the ion beam extractor, the unintended ions having diverged from a line from the target to the ion beam extractor, the unintended ions being obtained by ionizing elements of the target, out of ions in the vacuum vessel, the ion detector outputting a detection signal representing a value which is a number of the unintended ions or a mixing ratio of the unintended ions to the intended ions as a detection result, wherein the ion detector is disposed at a position diverged from the line from the target to the ion beam extractor so as not to interfere with the generated ion beam output to the external device; and
stopping the output of the ion beam when the value of the detection signal output from the ion detector is greater than a threshold value.

* * * * *